(12) United States Patent
Salahieh et al.

(10) Patent No.: US 7,648,518 B2
(45) Date of Patent: Jan. 19, 2010

(54) VASCULAR EMBOLIC FILTER DEVICES AND METHODS OF USE THEREFOR

(75) Inventors: Amr Salahieh, Saratoga, CA (US); Fred Khosravi, San Mateo, CA (US); Jackson Demond, Santa Cruz, CA (US); Jeff Krolik, Campbell, CA (US)

(73) Assignee: Incept LLC, San Mateo, CA (US)

( * ) Notice: Subject to any disclaimer, the term of this patent is extended or adjusted under 35 U.S.C. 154(b) by 505 days.

(21) Appl. No.: 11/219,033

(22) Filed: Sep. 1, 2005

(65) Prior Publication Data

US 2006/0004405 A1 Jan. 5, 2006

Related U.S. Application Data

(63) Continuation of application No. 10/001,396, filed on Oct. 18, 2001, now abandoned.

(51) Int. Cl.
*A61M 29/00* (2006.01)

(52) U.S. Cl. ........................ 606/200; 604/108

(58) Field of Classification Search ............... 606/200
See application file for complete search history.

(56) References Cited

U.S. PATENT DOCUMENTS

| | | | |
|---|---|---|---|
| 3,472,230 A | 10/1969 | Fogarty |
| 3,952,747 A | 4/1976 | Kimmell, Jr. |
| 3,996,938 A | 12/1976 | Clark, III |
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |

(Continued)

FOREIGN PATENT DOCUMENTS

WO 96/01591 A1 1/1996

*Primary Examiner*—Michael J Milano
*Assistant Examiner*—Victor X Nguyen
(74) *Attorney, Agent, or Firm*—Crompton, Seager & Tufte LLC (57) ABSTRACT

Vascular embolic filtering devices and systems, as well as methods for using the same, are provided. The embolic filtering device includes a guide wire and an associated embolic filter for capturing emboli created during interventional procedures within a target vessel. Features of the subject devices and system provide for delivering of the guide wire independently of the filter, rotating of the guide wire with respect to the filter and limiting or preventing the proximal translation of the filter with respect to the guide wire. The embolic filter is attached to a sheath having either a shorter-length configuration or an extended-length configuration. The guide wire comprises a proximal stop mechanism engageable with the sheath to limit at least the proximal translation of the embolic filter. The subject embolic filter systems provide such guide wires and embolic filters, as well as and an embolic filter delivery, deployment and removal assembly. The methods of the present invention provide for the use of the subject devices and systems.

12 Claims, 7 Drawing Sheets

U.S. PATENT DOCUMENTS

| | | | |
|---|---|---|---|
| 4,969,891 A | 11/1990 | Gewertz | |
| 5,011,488 A | 4/1991 | Ginsburg | |
| 5,071,407 A | 12/1991 | Termin et al. | |
| 5,133,733 A | 7/1992 | Rasmussen et al. | |
| 5,160,342 A | 11/1992 | Reger et al. | |
| 5,185,004 A | 2/1993 | Lashinski | |
| 5,192,286 A | 3/1993 | Phan et al. | |
| 5,324,304 A | 6/1994 | Rasmussen | |
| 5,329,942 A * | 7/1994 | Gunther et al. | 128/898 |
| 5,370,657 A | 12/1994 | Irie | |
| 5,415,630 A | 5/1995 | Gory et al. | |
| 5,419,774 A | 5/1995 | Willard et al. | |
| 5,462,529 A | 10/1995 | Simpson et al. | |
| 5,536,242 A | 7/1996 | Willard et al. | |
| 5,549,626 A | 8/1996 | Miller et al. | |
| 5,554,163 A | 9/1996 | Shturman | |
| 5,662,671 A | 9/1997 | Barbut et al. | |
| 5,669,933 A | 9/1997 | Simon et al. | |
| 5,769,816 A | 6/1998 | Barbut et al. | |
| 5,779,716 A | 7/1998 | Cano et al. | |
| 5,800,457 A | 9/1998 | Gelbfish | |
| 5,800,525 A | 9/1998 | Bachinski et al. | |
| 5,807,236 A | 9/1998 | Bacich et al. | |
| 5,807,398 A | 9/1998 | Shaknovich | |
| 5,814,064 A | 9/1998 | Daniel et al. | |
| 5,833,650 A | 11/1998 | Imran | |
| 5,848,964 A | 12/1998 | Samuels | |
| 5,911,734 A | 6/1999 | Tsugita et al. | |
| 6,066,149 A | 5/2000 | Samson et al. | |
| 6,066,158 A | 5/2000 | Engelson et al. | |
| 6,142,987 A | 11/2000 | Tsugita | |
| 6,152,946 A | 11/2000 | Broome et al. | |
| 6,168,579 B1 | 1/2001 | Tsugita | |
| 6,171,327 B1 | 1/2001 | Daniel et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,277,139 B1 | 8/2001 | Levinson et al. | |
| 6,344,049 B1 | 2/2002 | Levinson et al. | |
| 6,371,971 B1 | 4/2002 | Tsugita et al. | |
| 6,468,291 B2 | 10/2002 | Bates et al. | |
| 6,475,185 B1 | 11/2002 | Rauker et al. | |
| 6,537,296 B2 | 3/2003 | Levinson et al. | |
| 6,540,722 B1 | 4/2003 | Boyle et al. | |
| 6,599,307 B1 | 7/2003 | Huter et al. | |
| 6,605,102 B1 | 8/2003 | Mazzocchi et al. | |
| 6,616,681 B2 | 9/2003 | Hanson et al. | |
| 6,616,682 B2 | 9/2003 | Joergensen et al. | |
| 6,656,202 B2 | 12/2003 | Papp et al. | |
| 6,689,098 B2 | 2/2004 | Rauker et al. | |
| 6,695,813 B1 | 2/2004 | Boyle et al. | |
| 6,702,834 B1 | 3/2004 | Boylan et al. | |
| 6,706,055 B2 | 3/2004 | Douk et al. | |
| 6,726,701 B2 | 4/2004 | Gilson et al. | |
| 6,743,247 B1 | 6/2004 | Levinson et al. | |
| 6,773,448 B2 | 8/2004 | Kusleika et al. | |
| 6,878,291 B2 | 4/2005 | Lowe et al. | |
| 6,887,256 B2 | 5/2005 | Gilson et al. | |
| 6,893,451 B2 | 5/2005 | Cano et al. | |
| 6,902,572 B2 | 6/2005 | Beulke et al. | |
| 6,918,921 B2 | 7/2005 | Brady et al. | |
| 6,926,732 B2 | 8/2005 | Derus et al. | |
| 6,974,468 B2 | 12/2005 | DoBrava et al. | |
| 2001/0012951 A1 | 8/2001 | Bates et al. | |
| 2001/0041908 A1 | 11/2001 | Levinson et al. | |
| 2002/0026211 A1 | 2/2002 | Khosravi et al. | |
| 2002/0042626 A1 | 4/2002 | Hanson et al. | |
| 2002/0049467 A1 | 4/2002 | Gilson et al. | |
| 2002/0052626 A1 | 5/2002 | Gilson et al. | |
| 2002/0055747 A1 | 5/2002 | Cano et al. | |
| 2002/0058911 A1 | 5/2002 | Gilson et al. | |
| 2002/0062133 A1 | 5/2002 | Gilson et al. | |
| 2002/0095174 A1 | 7/2002 | Tsugita et al. | |
| 2002/0107541 A1 | 8/2002 | Vale et al. | |
| 2002/0120286 A1 | 8/2002 | DoBrava et al. | |
| 2002/0123720 A1 * | 9/2002 | Kusleika et al. | 604/108 |
| 2002/0161393 A1 | 10/2002 | Demond et al. | |
| 2002/0177872 A1 | 11/2002 | Papp et al. | |
| 2002/0183782 A1 | 12/2002 | Tsugita et al. | |
| 2003/0032977 A1 | 2/2003 | Brady | |
| 2003/0055483 A1 | 3/2003 | Gumm | |
| 2003/0078605 A1 | 4/2003 | Bashiri et al. | |
| 2003/0078614 A1 | 4/2003 | Salahieh et al. | |
| 2003/0130684 A1 | 7/2003 | Brady et al. | |
| 2003/0135232 A1 | 7/2003 | Douk et al. | |
| 2003/0139764 A1 | 7/2003 | Levinson et al. | |
| 2003/0144686 A1 | 7/2003 | Martinez et al. | |
| 2003/0144687 A1 | 7/2003 | Brady et al. | |
| 2003/0144688 A1 | 7/2003 | Brady et al. | |
| 2003/0144689 A1 | 7/2003 | Brady et al. | |
| 2003/0150821 A1 | 8/2003 | Bates et al. | |
| 2003/0153944 A1 | 8/2003 | Phung et al. | |
| 2003/0163064 A1 | 8/2003 | Vrba et al. | |
| 2003/0171770 A1 | 9/2003 | Kusleika et al. | |
| 2003/0208224 A1 | 11/2003 | Broome | |
| 2003/0212361 A1 | 11/2003 | Boyle et al. | |
| 2003/0212431 A1 | 11/2003 | Brady et al. | |
| 2003/0220665 A1 | 11/2003 | Eskuri et al. | |
| 2003/0225418 A1 | 12/2003 | Eskuri et al. | |
| 2003/0225435 A1 | 12/2003 | Huter et al. | |
| 2003/0229374 A1 | 12/2003 | Brady et al. | |
| 2004/0019363 A1 | 1/2004 | Hanson et al. | |
| 2004/0044360 A1 | 3/2004 | Lowe | |
| 2004/0087971 A1 | 5/2004 | Arnott | |
| 2004/0098032 A1 | 5/2004 | Papp et al. | |
| 2004/0116960 A1 | 6/2004 | Demond et al. | |
| 2004/0127934 A1 | 7/2004 | Gilson et al. | |
| 2004/0138692 A1 | 7/2004 | Phung et al. | |
| 2004/0138693 A1 | 7/2004 | Eskuri et al. | |
| 2004/0152941 A1 | 8/2004 | Asmus et al. | |
| 2004/0158280 A1 | 8/2004 | Morris et al. | |
| 2004/0164030 A1 | 8/2004 | Lowe et al. | |
| 2004/0167567 A1 | 8/2004 | Cano et al. | |
| 2004/0167568 A1 | 8/2004 | Boyle et al. | |
| 2004/0172055 A1 | 9/2004 | Huter et al. | |
| 2004/0199198 A1 | 10/2004 | Beulke et al. | |
| 2004/0220612 A1 | 11/2004 | Swainston et al. | |
| 2004/0260331 A1 | 12/2004 | D'Aquani et al. | |
| 2004/0267302 A1 | 12/2004 | Gilson et al. | |
| 2005/0004595 A1 | 1/2005 | Boyle et al. | |
| 2005/0010247 A1 | 1/2005 | Kusleika et al. | |
| 2005/0027236 A1 | 2/2005 | Douk | |
| 2005/0080356 A1 | 4/2005 | Dapolito et al. | |
| 2005/0080446 A1 | 4/2005 | Gilson et al. | |
| 2005/0096609 A1 | 5/2005 | Maginot et al. | |
| 2005/0125023 A1 | 6/2005 | Bates et al. | |
| 2005/0126979 A1 | 6/2005 | Lowe et al. | |
| 2005/0182440 A1 | 8/2005 | Bates et al. | |
| 2005/0187536 A1 | 8/2005 | Shelso et al. | |
| 2005/0209634 A1 | 9/2005 | Brady et al. | |
| 2005/0209672 A1 | 9/2005 | George et al. | |
| 2005/0222583 A1 | 10/2005 | Cano et al. | |
| 2005/0228437 A1 | 10/2005 | Gilson et al. | |
| 2005/0228471 A1 | 10/2005 | Williams et al. | |
| 2005/0234502 A1 | 10/2005 | Gilson et al. | |

* cited by examiner

VASCULAR EMBOLIC FILTER DEVICES AND METHODS OF USE THEREFOR

This application is a continuation application of U.S. application Ser. No. 10/001,396 as filed on Oct. 18, 2001 now abandoned.

INTRODUCTION

1. Field of the Invention

The present invention relates to devices and methods for filtering and removing matter from within the vasculature. More particularly, the invention is directed to a low-profile, self-expanding intravascular device useful for capturing emboli generated during interventional procedures, and for thrombectomy and embolectomy procedures.

2. Background of the Invention

Vascular procedures to treat occlusive vascular diseases, such as angioplasty, atherectomy and stent placement, often cause blood clots to form and/or material to dislodge from inside the vessel walls and enter the bloodstream. The dislodged material (e.g., plaque), known as emboli, may be large enough to occlude smaller downstream vessels, potentially blocking blood flow to tissue. Additionally, the blood clots, known as thrombi, may be large enough or grow over time to form a blockage at the interventional site or at another downstream location should the thrombus become released into the bloodstream. The resulting ischemia may pose a serious threat to the health or life of a patient if the blockage occurs in critical tissue, such as the heart, brain and lungs. Such blockages can lead to myocardial infarction and stroke.

Numerous previously known interventional systems and methods that employ an emboli filter mechanism have been proposed to reduce the risk of embolism. One such system includes an embolic filter system having a radially expandable mesh filter disposed on and fixed to the distal end of a guide wire. The filter is deployed distal to a region of stenosis, and an interventional device, such as an angioplasty balloon or a stent delivery system, is advanced along the guide wire. The filter is designed to capture emboli generated during treatment of the stenosis while permitting blood to flow through the filter.

Another similarly-functioning embolic protection device includes a guide wire and a filter comprised of a plurality of struts fixed to the distal end of the guide wire by means of the guide wire coil tip. The coil is wound about the periphery of the distal portion of the struts to fix the struts to the guide wire, forming a hinge-type connection by which the struts expand and close. A similar filter system includes a generally cone-shaped filter made of a porous polymer material. The distal end of the filter is securely fixed or formed to the system's guidewire.

With these conventional embolic filter systems, the filter mechanism is provided either permanently attached to or generally disposed on the distal end of the guide wire and, thus, is delivered simultaneously with the guide wire to the desired site within a vessel. Coupling the filter mechanism to the distal end of a guide wire serves to reduce the number of components in an embolic filtration system as well as the number of steps necessary to deliver and retrieve the components during intravascular procedures. Furthermore, without being fixed to the guide wire or at least restrained at the distal portion of the guide wire, a filter is able to move along the guide wire in both distal and proximal directions. This runs the risk of having the filter come off the distal end of the guide wire, leaving limited options for the safe retrieval of the filter from the patient's vasculature. There is also the risk of an unattached filter moving too far in the proximal direction and crossing back into the lesion, possibly interfering with the interventional procedure being performed.

Despite the advantages of attaching the filter to the guide wire, there are disadvantages of doing so. First and foremost, the attached filter increases the profile of the guide wire, making the initial crossing of the lesion more difficult particularly when the lesion is very narrow and tight. Additionally, with the filter fixed to the guide wire, there is a lack of independent rotational movement of the guide wire with respect to the filter. The lack of independent rotational movement of the guide wire increases the likelihood that the filter sac will become entangled around the guide wire.

It is desirable to have intravascular embolic protection systems that provide a guide wire without a permanently attached filter mechanism such that the guide wire may be delivered within the target vessel independently of the filter. Furthermore, it would be advantageous to have such devices and systems that provide for the independent rotational movement and some independent axial translation of the guide wire with respect to the filter. In addition, it is desirable that such devices and systems have the capability of limiting or preventing the axial translation of the filter with respect to the guide wire.

SUMMARY OF THE INVENTION

The present invention pertains to protection devices deployed in a body vessel or cavity for the collection of loosened or floating debris, such as embolic material dislodged during or thrombi formed as a result of an intravascular procedure. The subject invention is particularly helpful to protect the vasculature of a patient from dislodged emboli during angioplasty, atherectomy, thrombectomy, embolectomy, intravascular diagnostic and stent placement procedures.

Vascular embolic filtering systems and devices, as well as methods for using the same, are provided. In general, the subject systems include an independently deliverable guide wire and an associated embolic filter mechanism independently deliverable and retrievable over the guide wire. As such, a method of the subject invention provides for delivering a guide wire to a target location within a vessel distal to a lesion with the vessel and then delivering or tracking the filter mechanism over the delivered guide wire to a desired location at or adjacent the distal end of the guide wire.

Other features of the subject guide wires and filter mechanisms provide for the independent rotational movement of the guide wire with respect to the filter. The ability and flexibility to independently maneuver the guide wire and the filter facilitate the adjustment and optimal positioning of each. Furthermore, one can better ensure that the filter deploys properly and has a proper sealing engagement with the internal vessel wall throughout the procedure so as to reduce uncollected emboli.

The means for enabling axial translation and for independently rotating the guide wire with respect to the filter includes a sheath, preferably having a tubular configuration, to which the filter is attached. When operatively associated with the guide wire, this tubular sheath may be rotatably disposed about and along the guide wire. In other words, the guide wire is operatively disposed within a lumen of the tubular sheath. As such, when the filter is deployed within a vessel, and therefore substantially stationary at that location by the vessel wall pressure against the filter, it is relatively unaffected by axial translation of the guide wire. This independence of axial translation movement is particularly useful to prevent movement of the filter against the artery wall which causes trauma and damages the inner lining of artery.

In certain embodiments, the tubular sheath has a relatively short length that extends over no more than a portion of the distal end of the guide wire when the filter is operatively position. In other embodiments, the tubular sheath has a relatively long length such that, when the filter is operatively positioned towards the distal end of the guide wire, the tubular sheath extends proximally to outside the patient's body.

The tubular sheath enables the embolic filter to translate along the guide wire; however, the extent of translation, in both directions, is optimally limited or prevented. The means for limiting or preventing the axial translation of the filter includes at least one stop mechanism associated with the guide wire. This stop mechanism limits or prevents at least the proximal translation of the embolic filter with respect to the guide wire. In embodiments employing a short sheath, at least one stop mechanism is affixed to a distal end portion of the guide wire. In embodiments employing an extended length sheath, the proximal or first stop mechanism, is located at a proximal portion of the guide wire. These embodiments may further include a second or distal stop mechanism located distally to the respective first stop mechanism at a distal portion of the guide wire. This second or distal stop mechanism provides a point of enlargement that prevents an embolic filter from translating off the distal end of the guide wire. The point of enlargement is typically a metal bead soldered to the guide wire but may be any means for providing an enlargement over which the embolic filter cannot pass in the distal direction. The proximal stop includes a one-way translation member wherein the filter is able to translate along the guide wire from a location proximal to the proximal stop to a location distal to the proximal stop but is unable to then translate from the distal location back to the proximal location.

For embolic filter embodiments employing a shorter-length sheath, the proximal stop mechanism includes a one-way translation member affixed to the guide wire by means of a low-profile attachment point, for example, a solder bead, hinge or shrink tubing. The one-way translation member is configured to have a low-profile configuration, state, condition or position and a high-profile configuration state, condition or position. In the low-profile state, a filter is translatable over the one-way translation member and, in the high-profile state, a filter is prevented from translating over the one-way translation member in the proximal direction. A one-way translation member in a low-profile state preferably has a profile that is aligned longitudinally with the guide wire. The high-profile state preferably has a profile that creates a crosswise barrier along the guide wire.

In certain embodiments, the one-way translation member has a preformed configuration that is deformable to a low profile configuration and to a high profile configuration. Such embodiments may be made of a memory material such as nitinol. Deforming the one-way translation member to a low profile condition requires decreasing a dimension (e.g., the diameter or height) of the member that is normal to the longitudinal axis of the guide wire so that it becomes more flush or stream-line with the guide wire. Decreasing this dimension may require constricting, stretching or elongating the one-way translation member. On the other hand, deforming the member to a high profile condition may require increasing this dimension which may involve compressing the one-way translation member so as to create a barrier substantially normal to the longitudinal axis of the guide wire.

In other embodiments, the one-way translation member may be formed or made of a substantially fixed structure attached to the guide wire in a position or juxtaposition by a means, e.g., a spring-loaded hinge, that allows it to be reduced to a low-profile state. With either type of one-way translation member, the proximal stop is reducible to a low-profile state by an interventional device (e.g., a filter) disposed about the guide wire when moved from a position proximal of the proximal stop to a position distal of the proximal stop.

In the embodiments employing an extended-length tubular sheath, the means for limiting or preventing the axial translation of the filter includes a proximal stop mechanism preferably located at a proximal portion of the guide wire that extends outside the patient's body when the guide wire is operatively placed within the target vessel. The proximal stop mechanism includes means for locking the position of the sheath to which the filter is attached. When the position of the sheath is locked into place, the embolic filter is prevented from translating both proximally and distally and, thus, fixes the axial position of the embolic filter with respect to the guide wire. The means for locking the sheath includes a sleeve or the like placed circumferentially about the proximal end of the sheath and the guide wire, thereby holding the proximal portion of the sheath between the sleeve and the guide wire. The means for limiting or preventing may further include a second or distal stop mechanism similar to the one mentioned above.

BRIEF DESCRIPTION OF THE DRAWINGS

FIG. 1 includes FIGS. 1A-F which illustrate an one embodiment of an intravascular embolic filter system of the subject invention operatively employed, and a method for using the devices and systems of the present invention; wherein:

FIG. 2 includes FIGS. 2A-C which illustrate another embodiment of an intravascular embolic filter system of the subject invention operatively employed, and a method for using the devices and systems of the present invention; wherein:

FIG. 3 includes FIGS. 3A-C which illustrate another embodiment of an intravascular embolic filter system of the subject invention operatively employed, and a method for using the devices and systems of the present invention; wherein:

FIG. 4 includes FIGS. 4A-D, which illustrate another embodiment of an intravascular embolic filter system of the subject invention operably employed, and a method for using the device in systems of the present invention; wherein.

FIG. 5 includes FIGS. 5A-C which illustrate another embodiment of an intravascular embolic filter system of the subject invention operatively employed, and a method for using the devices and systems of the present invention; wherein:

DETAILED DESCRIPTION OF PREFERRED EMBODIMENTS

Exemplary embodiments of the present invention will now be discussed in detail.

I. Systems and Devices

The subject systems include a guide wire and an associated embolic filter for capturing emboli created during interventional procedures within a target vessel. The guide wires and embolic filters are not permanently fixed to each other and, thus, are independently deliverable and retrievable. They also provide for the independent rotational movement of the guide wire with respect to the filter and for enabling and limiting the axial translation of the filter along the guide wire. More specifically, the subject invention includes embolic filter assemblies comprising an embolic filter attached to an attachment sheath that is disposable, both rotationally and translationally, about the guide wire. Certain embodiments of the embolic filter assemblies employ relatively short attachment sheaths while other embodiments employ long attachment sheaths. Embodiments employing a relatively short attachment sheath also typically provide at least one stop mechanism located at a distal portion of the guide wire. This at least one stop mechanism prevents the undesired proximal translation of a filter assembly once operatively positioned at the distal end of the guide wire. Some embodiments employ a relatively long attachment sheath, i.e., one that extends proximally outside the body of the patient when operatively positioned in the vasculature. These latter embodiments typically employ a stop mechanism positioned towards the proximal end of the guide wire.

A. Embodiments Employing Short Filter Attachment Sheaths and Having a Distally-Positioned Stop Mechanism Referring now to FIGS. 1, 2, 3, and 4 wherein like components have like reference numbers, there are shown exemplary guide wire assemblies and embolic filter assemblies of the present invention employing relatively short filter attachment sheaths and at least one distally-positioned stop mechanism.

1. Guide Wire Assemblies

Illustrated in FIGS. 1A, 2A, 3A, and 4A guide wire assembly 10 includes a guide wire 12 having a flexible or floppy tip 16. Floppy tip 16 preferably has a spring or coiled configuration for facilitating the easy and efficient delivery of guide wire assembly 10 into a vascular system of a patient and across a lesion within the vasculature (not shown). Guide wire 12 is made of materials and has length and diameter dimensions commonly known in the art of intravascular procedures.

Guide wire assembly 10 also includes means associated with the guide wire to limit or prevent the axial translation of an interventional device, the means including by at least one stop mechanism generally located at a distal end portion 14 of guide wire 12. The at least one stop mechanism 20, referred to as a proximal stop mechanism, prevents an operatively placed device, such as a filter or filter assembly, from translating proximally beyond stop mechanism 20. Guide wire assembly 10 may also include a distal stop mechanism 18 positioned distally of proximal stop mechanism 20 to prevent an operatively placed filter or filter assembly from translating distally beyond distal stop mechanism 18. Together the two stops 18, 20 define a translation segment or deployment region 19 of guide wire 12 there between along which an embolic filter may be translated and deployed.

Distal stop 18 is a point of enlargement located and fixed at the distal portion 14 of guide wire 12. This point of enlargement may be a solder bead or 30 other means for enlarging a distal point of guide wire 12. Proximal stop 20 includes a one-way translation member, referenced as 22 in FIG. 1, 60 in FIG. 2, 70 in FIG. 3 and 20 in FIG. 4, fixed to guide wire 12 by means of fixation point 24 at a location proximal to distal stop 18. Fixation 24 may comprise, for example, a solder bead, similar to that of distal stop 18 of FIGS. 1, 2 and 4 or the hinge pin of FIG. 3.

a. Deformable Proximal Stop Mechanisms

The proximal stop embodiments of FIGS. 1 and 2 have a deformable one-way translation member. More specifically, these respective one-way translation members have a preformed or original configuration having a wire component that is deformable to a constricted or low profile configuration and also to an expanded or high profile configuration. The low profile configuration allows continued translation of a device, such as a filter, filter assembly, sheath, tube or other medical device, tracked over guide wire 12 in the distal direction. The expanded, high profile configuration is formed when a device is translated along guide wire 12 in a proximal direction and is caused to abut against the one-way translation member. The high profile configuration creates a cross-wise barrier substantially normal to the longitudinal axis of the guide wire to prevent further proximal translation of the device.

In the embodiment of FIG. 1, one-way translation member 22 has wire strands 23 that distally extend a short distance from attachment point 24. Although two wire strands 23 are shown, one-way translation member 22 may have only one wire strand or any other appropriate number of wire strands. Wire strands 23 are preferably formed of a super-elastic material, such as a nickel-titanium alloy ("Nitinol"). As such, wire strands 23 have a preformed configuration, as shown in FIGS. 1A and 1E, which may have any appropriate configuration that can be constricted within a small diameter sheath as well as expanded to a diameter that is large enough to create a barrier to devices moving from the distal side of the proximal stop to the proximal side of the proximal stop but small enough so as not to cause injury to the internal wall of the vessel. Each wire strand 23 has a preformed "elbow" configuration that provides a spring-like action. The preformed configuration is constrictable to an elongated, low profile configuration, as shown in FIGS. 1B, C and D, as well as compressible to an expanded, high profile configuration, as in FIG. 1F. The elongated, low profile configuration is formed when a device, such as a sheath or a tube, is translated along guide wire strand 12 and over wire strands 23 in a distal direction.

Figure 1A:
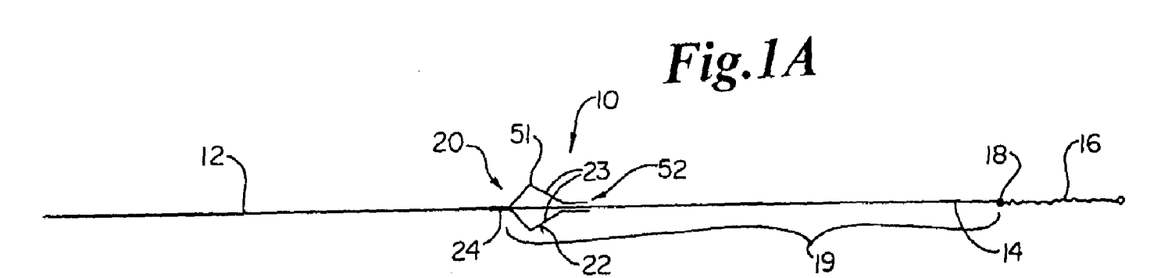
FIG. 1A illustrates one embodiment of a guide wire assembly of the present invention having a guide wire and an axial movement limitation system for limiting the axial movement of a filter operatively engaged with the guide wire, the axial movement limitation system including a proximal stop mechanism and a distal stop mechanism, the proximal stop mechanism having distally-extending wire strands shown in a preformed state.
Figure 1B:
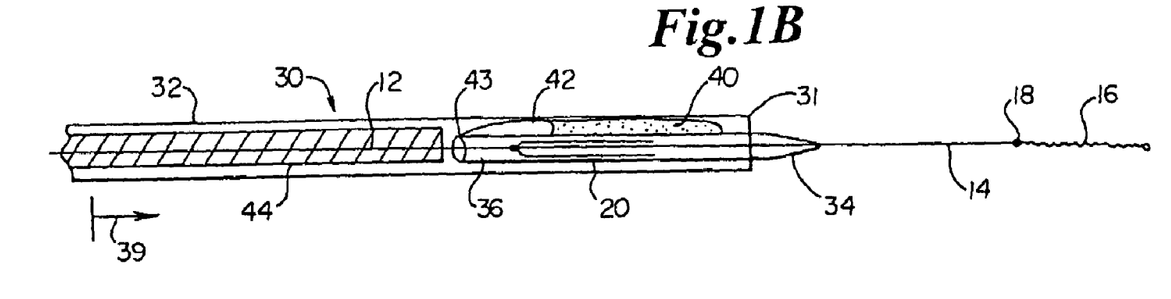
FIG. 1B illustrates the guide wire assembly of FIG. 1A and an embolic filter delivery, deployment and removal assembly operatively disposed about the guide wire wherein the delivery, deployment and removal assembly includes an embolic filter assembly having means for rotational movement about the guide wire; the filter assembly is being delivered over the guide wire in a distal direction, crossing over the proximal stop mechanism and compressing it into a low-profile state.
Figure 1C:
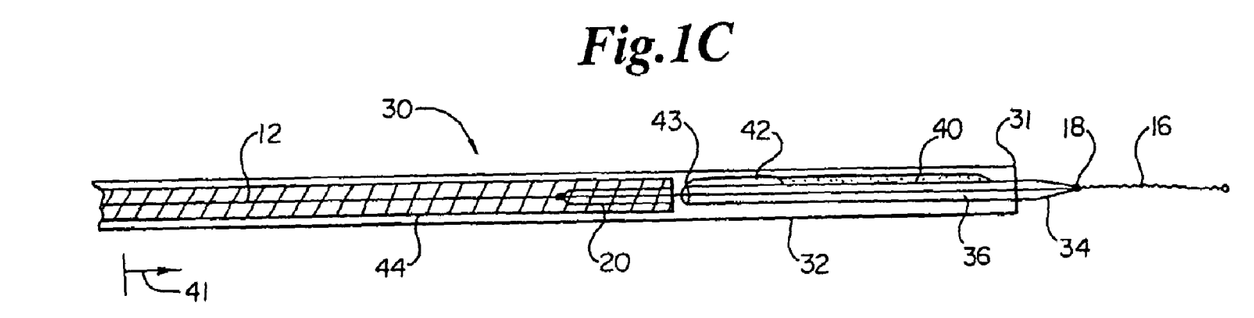
FIG. 1C illustrates the same guide wire assembly and embolic filter delivery, deployment and removal assembly operatively engaged as in FIG. 1B wherein the delivery, deployment and removal assembly has been further advanced in a distal direction such that the distal tip of the embolic filter assembly abuts the distal stop mechanism.
Figure 1D:
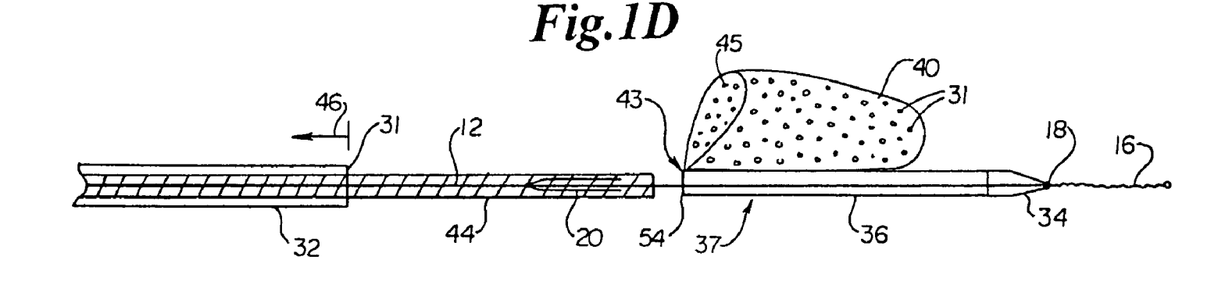
FIG. 1D illustrates the same operative engagement wherein a delivery sheath of the embolic filter delivery, deployment and removal assembly is being pulled proximally away from the remainder of the assembly such that the embolic filter has been operatively deployed and a rotatable filter attachment tube abuts the distal stop which prevents further advancement of the filter assembly in the distal direction.
Figure 1E:
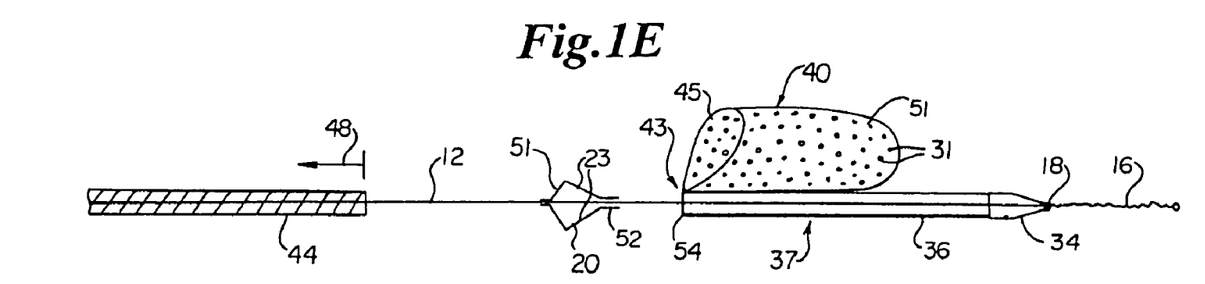
FIG. 1E illustrates the distal removal of a pusher mechanism such that the proximal stop mechanism has been operatively deployed to a high-profile state to prevent proximal movement of the embolic filter assembly of FIG. 1D along the guide wire past the proximal stop mechanism.
Figure 1F:
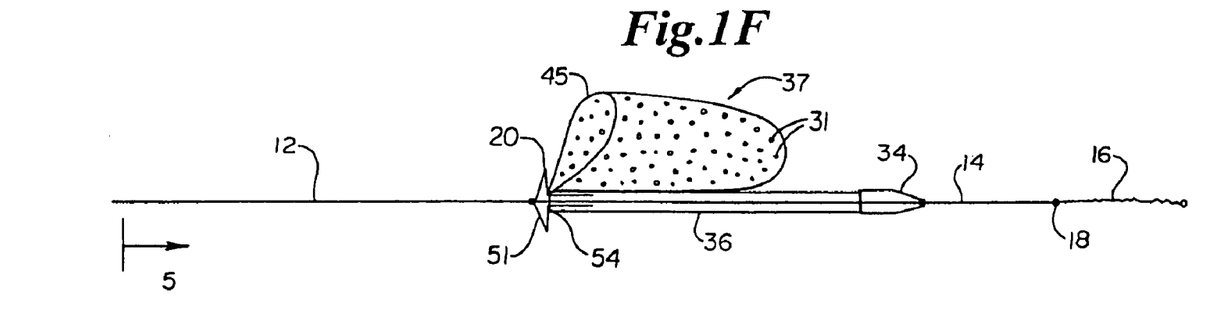
FIG. 1F illustrates the proximal end of the embolic filter assembly of FIG. 1D abutting the proximal stop mechanism and thereby being prevented from further axial movement in the proximal direction.
Figures 1G, 2A:
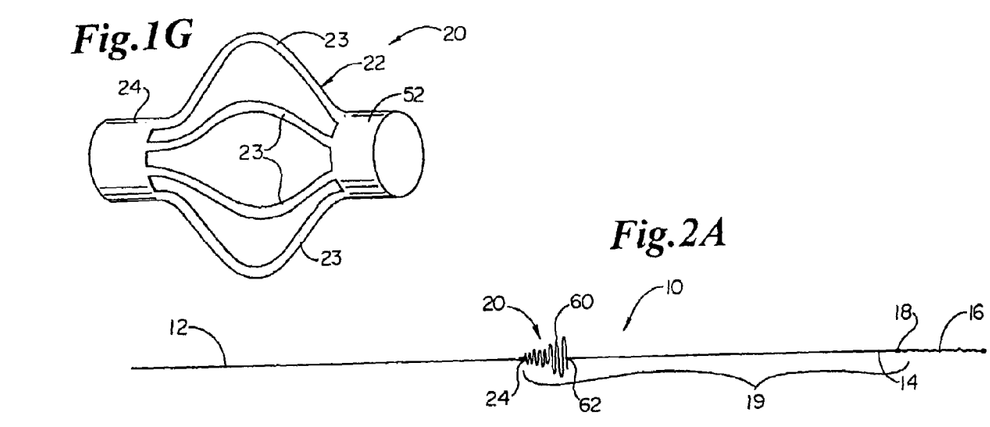
FIG. 1G illustrates an alternate embodiment of the proximal stop mechanism.
FIG. 2A illustrates a guide wire assembly of the present invention having a guide wire and another embodiment of an axial movement limitation system for limiting the axial movement of a filter operatively engaged with the guide wire, the axial movement limitation system having a proximal stop mechanism having a distally-extending, coiled spring configuration shown in its preformed state.

As an alternate to stop 20 of FIG. 1A, stop 20 of FIG. 1G could be affixed to wire 12 at attachment point 24. Stop 20 of FIG. 1G can be formed from, for example a laser cut hypotube. Laser cutting can form strands 23 between proximal attachment point 24 at a distal end 52 of strands 23. At both attachment point 24 and distal end 52 a cylindrical portion of the laser cut hypo tube can remain. The cylindrical portion at proximal attachment point 24 can be soldered to the guide wire, whereas the cylindrical portion at distal 52 can be free to slide proximally and distally on guide wire 12. Strands 23 are preferably bent outward as shown in FIG. 1G when in a relax state. The hypo tube can be formed from stainless steel, nickel titanium alloy ("Nitinol") or other suitable material.

Figure 2B:
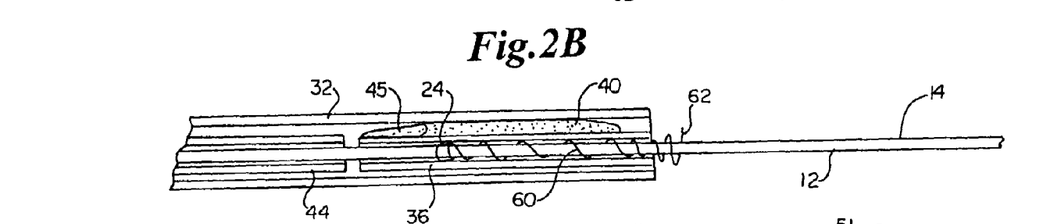
FIG. 2B illustrates an enlarged longitudinal cross-sectional view of a distal portion of the guide wire assembly of FIG. 2A and the embolic filter delivery, deployment and removal assembly of FIG. 1 being delivered over the guide wire in a distal direction, crossing over the proximal stop mechanism and compressing the coiled spring into a low-profile state.
Figure 2C:
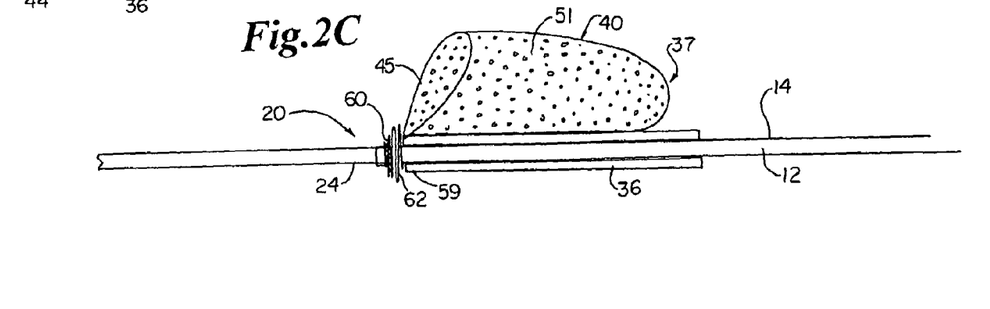
FIG. 2C illustrates the same distal portion of the guide wire assembly of FIG. 2A and the embolic filter assembly of FIG. 1, wherein the embolic filter assembly has been operatively placed distal to the proximal stop and is prevented from axial movement in the proximal direction such that the proximal tip of the embolic filter assembly abuts the proximal stop mechanism, causing it to expand into a high-profile state.

In the embodiment of FIG. 2, one-way translation member 60 is a coiled wire attached to and extending distally from solder bead 24. As shown in FIG. 2A, coil 60 is in a deployed or biased, preformed state wherein coil 60 has a diameter that increases distally to a maximum diameter at distal end 62. The maximum diameter of coil 60 is great enough to snuggly contact the internal vessel wall. FIG. 2B illustrates coil 60 in an undeployed or constricted, low profile state within filter attachment tube 36 such that coil 60 is stretched until distal end 62 achieves a diameter that allows it to pass within the lumen of filter attachment tube 36. FIG. 2C illustrated coil 60 when in a high profile state caused by the compressive force applied by filter assembly 37 when proximally advanced. The high profile state provides a cross-wise barrier to devices moving from the distal side of coil 60 to the proximal side of coil 60.

b. Fixed Configuration Proximal Stop Mechanisms

Figure 3A:
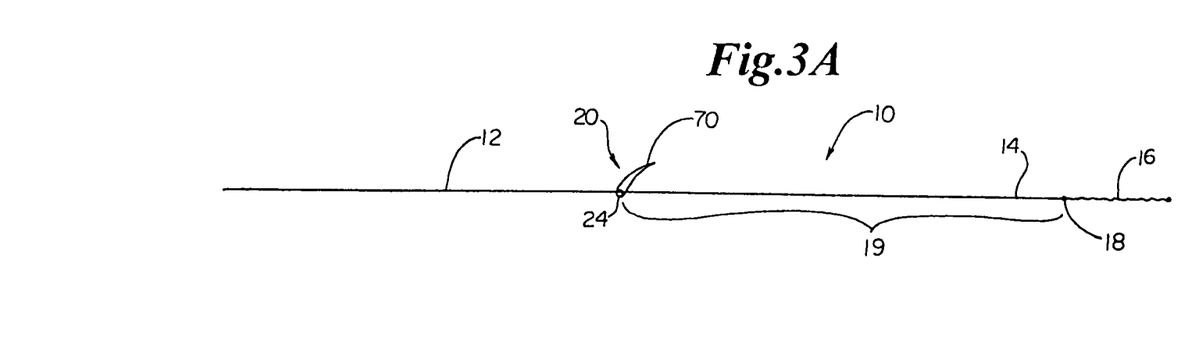
FIG. 3A illustrates a guide wire assembly of the present invention having a guide wire and another embodiment of an axial movement limitation system for limiting the axial movement of a filter operatively engaged with the guide wire, the axial movement limitation system having a proximal stop mechanism having a retractable member, shown in a deployed state.
Figure 3B:
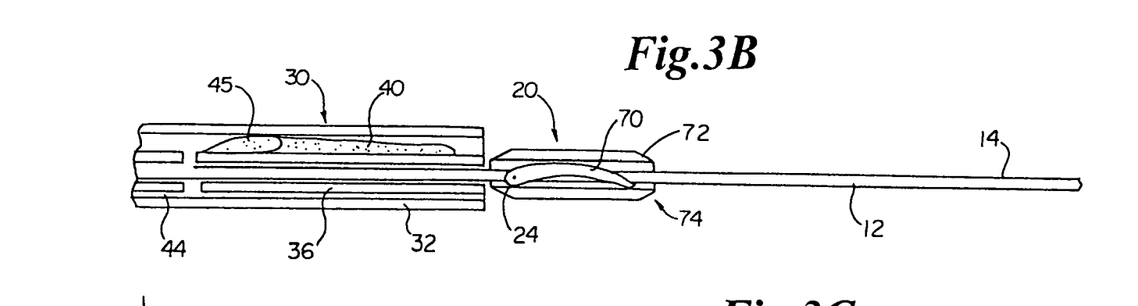
FIG. 3B illustrates an enlarged longitudinal cross-sectional view of a distal portion of the embolic filter delivery, deployment and removal assembly of FIGS. 1 and 2 disposed over the guide wire assembly of FIG. 3A which further includes a protective sheath operatively disposed about the guide wire and the proximal stop mechanism such that the retractable member is in an undeployed state.
Figure 3C:
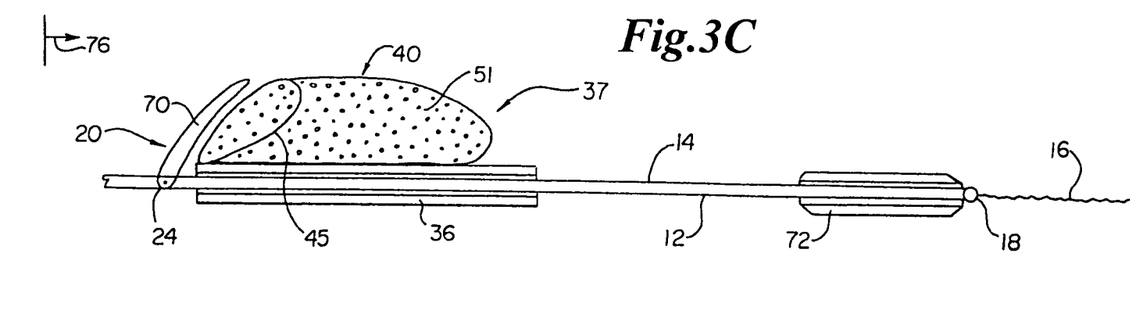
FIG. 3C illustrates the same distal portion of the guide wire assembly of FIG. 3B after the delivery, deployment and removal assembly has been advanced distally so as to distally advance the protective sheath and the embolic filter assembly distally of the retractable member and after proximal removal of the delivery, deployment and removal assembly sheath such that the embolic filter and retractable member have achieved respective deployed states.
Figure 4A:
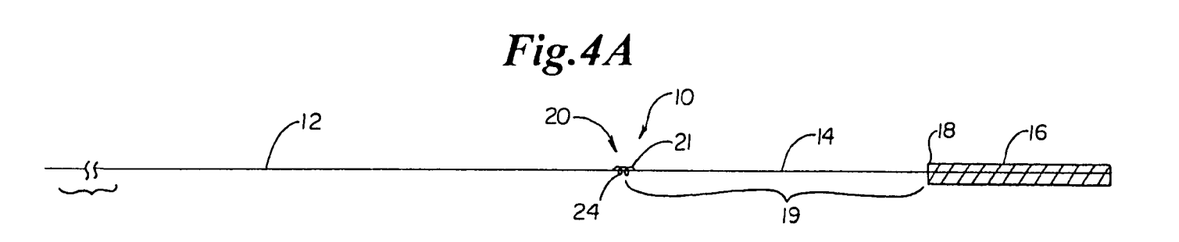
FIG. 4A illustrates a guide wire assembly of the present invention having a guide wire and another embodiment of an axial movement limitation system for limiting axial movement of a filter operably engaged with the guide wire; the axial movement limitation system having a proximal stop mechanism having a male thread feature.
Figure 4B:
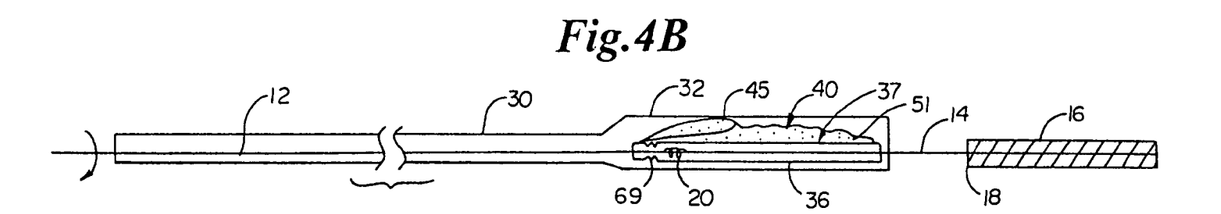
FIG. 4B illustrates an enlarged longitudinal cross-sectional view of a distal portion of the embolic filter delivery, deployment and removal assembly exposed over the guidewire assembly of FIG. 4A, including a female threaded feature disposed proximally of the male threaded feature.
Figure 4C:
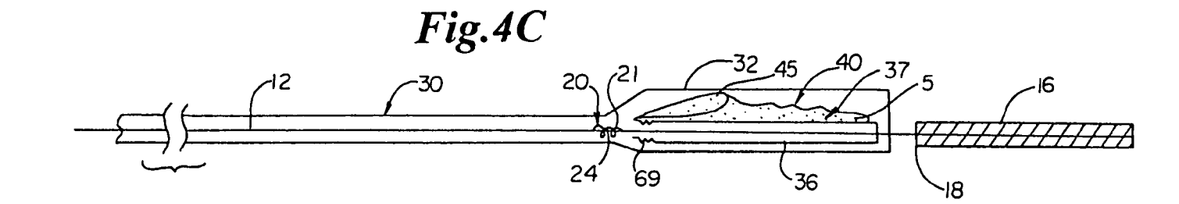
FIG. 4C illustrates an enlarged longitudinal cross-sectional view of a distal portion of the embolic filter delivery, deployment and removal assembly disposed over the guidewire assembly of FIG. 4A, which further includes a protective sheath including the female threaded feature disposed distally of the male threaded feature.
Figure 4D:
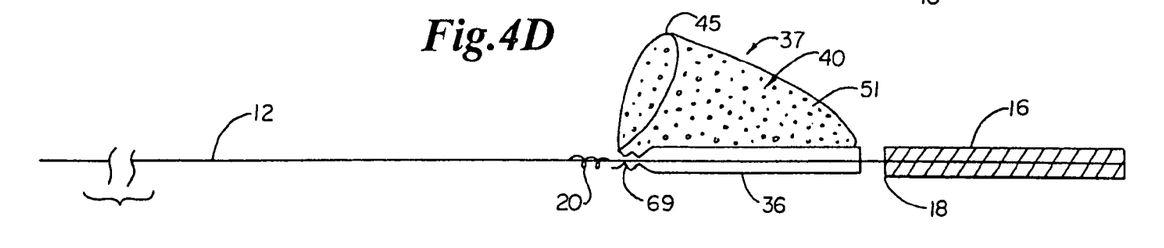
FIG. 4D illustrates the same distal portion of the guidewire assembly of FIG. 4C after proximal removal of the delivery, deployment and removal assembly sheath such that the embolic filter has achieved the deployed state.

Referring now to FIG. 3, there is illustrated another embodiment of a proximal stop 20 including a one-way translation member 70 pivotally attached to guide wire 12 by means of a hinge mechanism 24. The one-way translation member has a substantially fixed configuration in the form of a lever or pivot member 70, for example. Member 70 may be a made of a solid piece of material, such as stainless steel or a biocompatible plastic, or may be made of a wire conformed to define the desired outline of member 70. Member 70 has a naturally deployed or biased, high profile state, as shown in FIGS. 3A and C, and an undeployed or unbiased, low profile state as shown in FIG. 3B. Hinge mechanism 24 provides a spring-bias to lever member 70 such that lever member 70 is naturally biased in a high profile state at an angle α with guide wire 12 and spring-loaded when in a low profile state.

When a device, such as a filter, filter assembly, sheath, tube or other medical device, is caused to pass over proximal stop 20 in the distal direction, lever member 70 is caused to rotationally pivot about hinge 24 and become substantially coaxially aligned with guide wire 12, achieving a low profile state. As soon as the device completely passes over the distal tip of lever member 70, lever member 70 springs back to its biased, high profile state. As such, when the device is then translated back in the proximal direction, the device is prevented from further proximal translation by proximal stop 20 (see FIG. 3C).

In order to minimize the risk of trauma to the patient's vessel and/or the dislodgment of emboli while delivering guide wire assembly 10 of FIG. 3 to a target site within the patient's vasculature, a protective sheath 72 is disposed about proximal stop 20 to retain lever member 70 in a low profile state. Protective sheath 72 has an inner lumen diameter sized to allow sheath 72 to be easily pushed over lever member 70 while being snug enough to remain in position over lever member 70 when guide wire assembly is being delivered to or retrieved from the vessel. Protective sheath 72 has a length that preferably extends the length of lever member 70, but may be longer or shorter, and has tapered or beveled proximal and distal ends 74 to further facilitate the atraumatic delivery of guide wire assembly 10.

FIG. 4 illustrates another embodiment of proximal stop 20 including a male threaded feature 21 fastened to wire 12. Male threaded feature 21 can be formed from, for example, a wire helix disposed on wire 12. The wire helix can be connected to wire 12 by adhesive, solder or other suitable means. Floppy tip 16 can include a coil acting as a distal stop.

The configurations of the proximal stop mechanisms illustrated and described herein are intended to be exemplary and are not intended to limit the configuration of the proximal stop mechanism of the present invention. Any other suitable configuration, such as a distally opening umbrella configuration, may be employed to provide the functions as described above.

2. Filter Delivery, Deployment and Removal Assembly

The structure of an exemplary filter delivery, deployment and removal assembly 30 of the present invention, such as those disclosed in co-owned U.S. Pat. Nos. 6,129,739 and 6,179,861 B1, both entitled "Vascular Device Having One or More Articulation Regions and Methods of Use, hereby incorporated by reference, will now be described. An exemplary filter delivery, deployment and removal assembly 30 includes an embolic filter assembly 37 (see FIGS. 1D-F, 2B, 3B, and 4B-C), a pusher tube 44 and a delivery sheath 32. Delivery sheath 32 and pusher tube 44 have length dimensions such that their proximal ends extend from the vascular access site when their distal ends are in the vicinity of the lesion within the target vessel. When operatively engaged, filter assembly 37 and the distal end of pusher tube 44 are positioned co-axially within distal end 31 of the lumen of delivery sheath 32, wherein filter assembly 37 is positioned distally with respect to pusher tube 44. Pusher tube 44 is used to push or advance filter assembly 37 distally along guide wire 12 while delivery sheath 32 is also being advanced distally along guide wire 12. In FIG. 4, sheath 32 itself acts as the pusher.

Filter assembly 37 includes a filter 40 attached along the length of a filter attachment tube 36 (see FIGS. 1D-F, 2B-C, 3B-C, and 4B-D). Filter attachment tube 36 has open proximal and distal ends and a guide wire lumen there between and, as such, is engageable and positionable co-axially about guide wire 12. Tube 36 provides for the independent rotational and translational movement of filter 40 with respect to guide wire 12. The rotational capabilities of filter attachment tube 36 help to mitigate the unintentional twisting of filter 40 about guide wire 12 which can commonly occur upon rotational movement of guide wire 12. Attachment tube 36 also provides for the ability of filter assembly 37 to translate axially along guide wire 12, however, this translational movement is limited by the axial translation limitation system (i.e., distal stop 18 and proximal stop mechanism 20) mentioned above, and discussed in further detail below. Although filter attachment tube 36 is illustrated having a tubular configuration, any configuration which allows guide wire 12 to translate and rotate freely through the sheath may be used with the present invention. Attachment tube 36 of FIG. 4 includes a female threaded portion which can be, for example, disposed at tube 36 proximal end.

Preferably, filter attachment tube 36 is made of a flexible material, such as a polymer, including but not limited to polyamide or polytetraethylene, to facilitate translational movement through curvaceous vessel anatomy. In the embodiment of FIG. 1, nose cone 34 is mounted to the distal end of filter attachment tube 36 and extends distally beyond the distal end of delivery sheath 32 in order to facilitate atraumatic tracking of tubular tube 36 and filter delivery, deployment and retrieval assembly 30 through the target vessel.

Filter 40 includes a support hoop 45 and a blood-permeable sac 51 attached thereto and, as such, support hoop 45 forms a mouth or proximal opening of sac 51 while sac 51 provides a closed but permeable distal end. Support hoop 45 is attached to the proximal end 43 of tubular tube 36 such that sac 51, in either a deployed or compressed state, lies generally axially along tubular tube 36. Preferably, support hoop 45 is formed of a super-elastic material, such as Nitinol, and as such has a constrictable, preformed state. Support hoop 45 is capable of folding or being constricted to fit into small diameter delivery sheath 32. When filter 40 is in a deployed state, as depicted in FIGS. 1D-F, 2C, 3C, and 4D support hoop 45 resumes its preformed configuration, forming an open proximal end or mouth. Support hoop 45 may have a variety of other features, as disclosed in U.S. Pat. No. 6,129,739, which enhance its performance.

Sac 51 is preferably constructed of a thin, flexible biocompatible material, such as a polymer material including, for example, polyethylene, polypropylene, polyurethane, polyester, polyethylene tetraphlalate, nylon or polytetrafluoroethylene, or combinations thereof. Sac 51 includes openings or pores 31 that permit blood cells to pass through the sac substantially unhindered, while capturing any larger emboli that may be released during an intravascular procedure. These pore sizes will permit red blood cells to easily pass through sac 51. Sac 51 may alternatively comprise a woven material, such as formed from the above-mentioned polymers, in which case the pore size of the sac may be determined as a function of the pattern and tightness of the weave.

Delivery sheath 32 has an open distal end 31 which is sufficiently tapered (not shown) to reduce the risk of injury to a patient's vessel or of inadvertently becoming entangled with a placed stent (a concern when delivery sheath 32 is used to retrieve the filter assembly after completion of a stent placement procedure). The inner diameter of delivery sheath 32 is sufficiently large to allow nose cone 34 (shown in FIGS. 1B-E; discussed in detail below) of filter attachment tube 36 of filter assembly 37 to extend distally from the opening, but sufficiently small to prevent the distal advancement of filter attachment tube 36 beyond the opening. Alternatively, open distal end 31 may have an inwardly-extending lip (not shown)

to form an opening having a diameter which meets the same requirements. Delivery sheath 32 has a relatively narrow configuration for fitting through tight and tortuous vessel anatomy. Both filter attachment tube 36 and pusher tube 44 have inner diameters, respectively, capable of accommodating guide wire 12 and proximal stop 20. As mentioned above, pusher tube 44 has a length that extends outside the vascular access when operatively positioned at the delivery site within the target vessel, and thus its length will depend on the length of the particular vascular delivery path into which it is employed.

It can be appreciated that in yet another alternate embodiment of the invention, proximal stop 20 need not be included on wire 12. In such a configuration, pusher tube 44 can be used to hold filter assembly 37 at the distal end of guide wire 12 against distal stop 18. Then sheath 32 can be withdrawn proximately to deploy filter assembly 37 on the wire.

In yet another alternate embodiment, sheath 32 can be tapered inwardly just proximately of filter assembly 37 to engage proximal end 43. In this configuration, filter assembly 37 can be delivered to distal stop 18 without pusher tube 44. Once filter assembly 37 is positioned distally of stop 20, sheath 32 can be withdrawn proximately to deploy filter assembly 37.

B. Embodiments Employing Extended-Length Filter Attachment Sheaths and Having a Proximally-Positioned Stop Mechanism Referring now to FIGS. 5, 6 and 7, wherein like components have like reference numbers, there is shown another embolic filter system of the present invention. In accordance with the present invention, this embolic filter system also provides for the independent delivery of the guide wire with respect to the embolic filter. Additionally, other features provide for the independent rotational movement of the guide wire with respect to the filter and for the enablement and limitation of the axial translation of the filter along the guide wire for the purpose of optimally positioning or adjusting the guide wire and/or the filter during an interventional procedure.

Figure 5A:
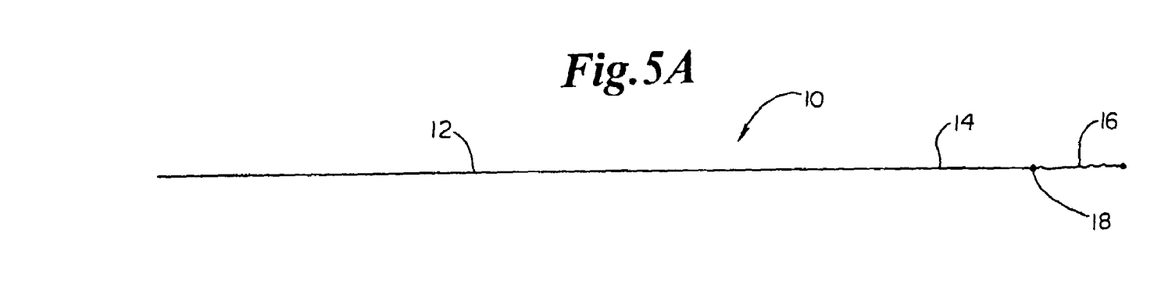
FIG. 5A illustrates another embodiment of an independently deliverable guide wire of the present invention.

In FIG. 5A, there is shown a guide wire assembly 10 having a guide wire 12, a distal stop mechanism in the form of solder bead 18, and a floppy tip 16 extending distally from solder bead 18. Without a permanently attached filter, the profile of guide wire assembly 10 is kept low which is advantageous when negotiating tortuous vasculature and particularly when crossing a lesion. Guide wire 12 is preferably made of the materials discussed above with respect to FIG. 1.

Figure 5B:
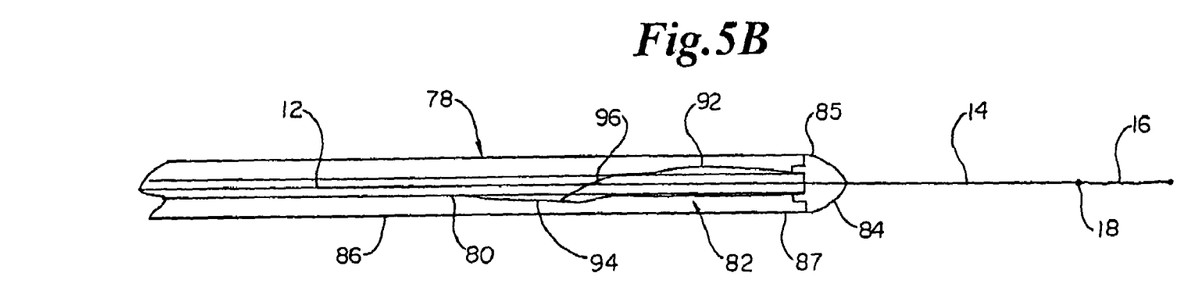
FIG. 5B illustrates another embodiment of a delivery, deployment and retrieval assembly of the present invention operatively disposed over the guide wire of FIG. 5A.
Figure 5C:
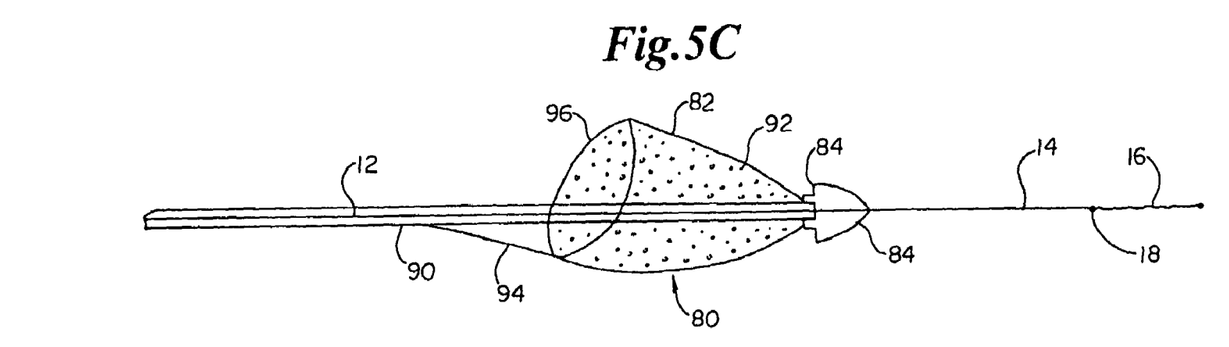
FIG. 5C illustrates another embodiment of an embolic filter assembly of the present invention having an extended-length tubular sheath operatively disposed over the guide wire of FIG. 5A.

As best illustrated in FIG. 5C, there is shown another exemplary embolic filter assembly 80 of the present invention operatively disposed on the distal end 14 of guide wire 12. Filter assembly 80 includes an embolic filter 82 operatively attached to filter attachment sheath 90. Here, filter 82 has a strut-type configuration such as those disclosed in co-owned and co-pending U.S. patent application Ser. No. 09/764,774, entitled "Vascular Device for Emboli Removal Having Suspension Strut and Methods of Use" and filed on Jan. 16, 2001, hereby incorporated by reference. Generally, filter 82 includes a blood-permeable sac 92 affixed at its perimeter to a self-expanding support hoop 96 mounted to a flexible suspension strut 94 which in turn is affixed to filter attachment sheath 90 at a point proximal to filter 82. Suspension strut 94 permits guide wire 12 to rotate and move laterally relative to support hoop 96 without the support hoop becoming disengaged from the vessel wall when in a deployed state. Sac 92 and support hoop 96 are preferably made of the materials mentioned above of with respect to sac 51 and support hoop 45, respectively. Suspension strut 94 may be made of the same materials used for the support hoops.

Unlike filter attachment tube 36 discussed with respect to FIGS. 1, 2, 3, and 4 filter attachment sheath 90 has a length which, when operatively disposed over guide wire 12, extends proximally from nose cone 84 to outside the patient's body. Thus, extended-length filter attachment sheath 90 is itself used, rather than the pusher tube discussed above with respect to the embodiments of FIGS. 1, 2 and 3, to deliver and remove filter assembly 80, as well as to rotate and axially translate filter assembly 80 with respect to guide wire 12.

Similar to the shorter-length filter attachment sheath, filter attachment sheath 90 has a tubular configuration positioned co-axially about guide wire 12 and, as such, provides for the independent rotational movement of filter 82 with respect to guide wire 12. The rotational capabilities of filter attachment sheath 90 help to mitigate the unintentional twisting of filter 82 about guide wire 12 which can commonly occur upon rotational movement of guide wire 12. As sheath 90 is not permanently attached to guide wire 12, it also provides for the ability of filter assembly 80 to translate axially along guide wire 12, however, this translational movement may be limited or prevented altogether by the means for limiting or preventing the axial translation, discussed in detail below with respect to FIGS. 6 and 7.

FIG. 5B illustrates an embolic filter delivery, deployment and retrieval assembly 78 operatively disposed over guide wire 12 and filter assembly 80. Assembly 78 includes a delivery sheath 86 for maintaining filter 82 in an undeployed condition while delivering filter assembly 80 to distal end portion 14 of guide wire 12. A nose cone 84 is mounted to the distal end of attachment sheath 90 and has an extended lip 85 that is positionable over the distal end 87 of delivery sheath 84 to facilitate the atraumatic tracking of assembly 78 over guide wire 12. The components of filter delivery, deployment and retrieval assembly 78 are preferably made of the materials mentioned with respect to the respective corresponding components of the embodiment of FIGS. 1, 2, 3, and 4.

Figure 6:
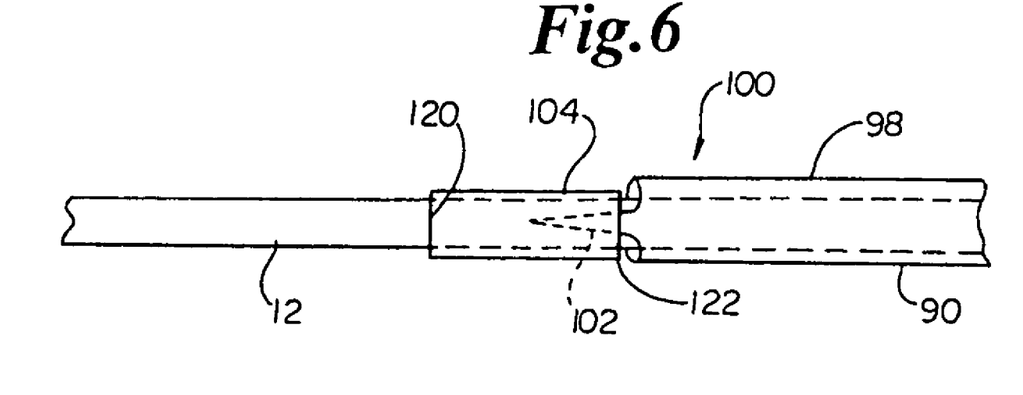
FIG. 6 illustrates an embodiment of an axial translation limitation or prevention system employing a proximal stop mechanism or means for locking the axial position of the tubular sheath of FIG. 5 with respect to the guide wire, the means or mechanism including a snuggly-fitted sleeve.
Figure 7:
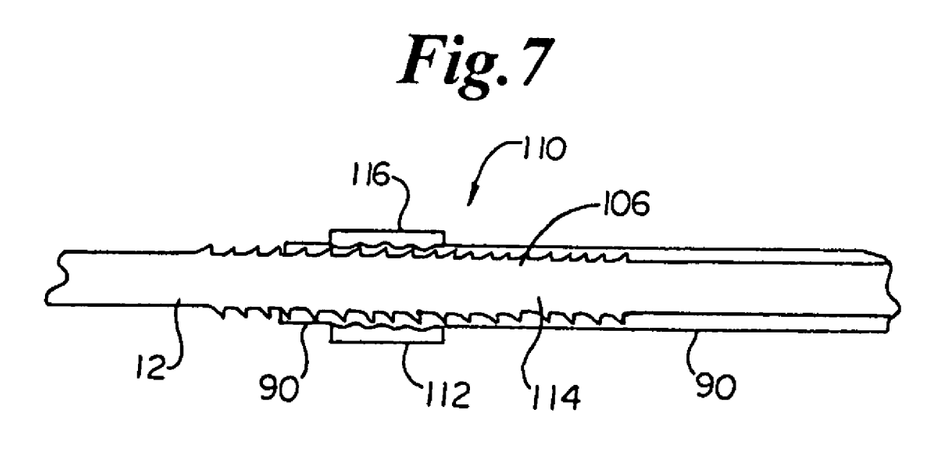
FIG. 7 is illustrates another embodiment of an axial translation limitation or prevention system employing a proximal stop mechanism or means for locking the axial position of the tubular sheath of FIG. 5 with respect to the guide wire, the means or mechanism including a threaded sleeve.

Referring now to FIGS. 6 and 7, there are shown two embodiments of the axial translation limitation or prevention systems of the subject invention for use with the embolic filter system of FIG. 5. FIG. 6 shows an enlarged view of proximal end 98 of extended-length attachment sheath 90. The axial translation limitation or prevention system provides a stop mechanism 100 associated with a proximal portion of guide wire 12 and the distal end of extended-length sheath 90 for limiting both the proximal and the distal axial translation of sheath 90 and filter assembly 80. Stop mechanism 100 and includes a cuff or sleeve 104 disposed about guide wire 12 and a tapered end portion 102 of sheath 90. At its proximal end 120, sleeve 104 fits snugly about guide wire 12 and has a slightly increasing diameter towards its distal end 122. As such, tapered portion 102 is slideable into distal end 122 and firmly securable between sleeve 104 and guide wire 12, thereby preventing any proximal and distal translation of extended-length sheath 90 and, thus, temporarily fixing or locking the position of filter assembly 80 with respect to guide wire 12. The limitation and prevention system may further include a distal stop mechanism such as that discussed above with respect to FIGS. 1-4. Attachment sheath 90 may be unlocked and relocked throughout the procedure as necessary for axial or rotational repositioning. Sleeve 104 is preferably made of a flexible material including, but not limited to, a polymer. Sleeve 104 may be permanently affixed to the proximal portion of guide wire 12 such as by means of shrink tubing or a compressive ring or cuff. Alternately, sleeve 104 may be frictionally slideable or moveable along guide wire 12 so as to be positionable as desired.

FIG. 7 is an enlarged view of a longitudinal cross-section of an alternate embodiment of an axial translation limitation or prevention system for use with the embolic filter system of FIG. 5. The system includes a stop mechanism 110 located at a proximal portion of guide wire 12 for limiting or preventing the proximal and distal axial translation of sheath 90 and filter assembly 80. Here, stop mechanism 110 includes a threaded portion 106 of the proximal end of guide wire 12, having threads which are engageable with corresponding threads on the lumen of a threaded collar or sleeve 116. Threaded sleeve 116 is preferably made of stainless steel or other approved material. Threaded portion 106 may extend any suitable distance along the proximal end of guide wire 12 in order to optimize the axial position of attachment sheath 90 with respect to guide wire 12. When positioned over threaded portion 106, distal end 98 of extended-length attachment sheath 90 can be locked at that location by means of threaded collar 116. As such, embolic filter assembly 80 is prevented from translating proximally and distally as desired, and attachment sheath 90 may be unlocked and relocked throughout the procedure as necessary for repositioning of embolic filter assembly 80. The limitation and prevention system may further include a distal stop mechanism such as that discussed above with respect to FIGS. 1-4.

II. Methods

The methods of using the subject embolic filter systems and their associated components will now be described in the context of an intravascular procedure, such as an angioplasty, atherectomy, thrombectomy, stent placement or intravascular diagnostic procedure, to treat and diagnose a lesion within a target vessel, such as a coronary artery, a carotid artery or a bypass graft vessel, such as a saphenous vein graft.

A. Short Tubular Filter Attachment Sheath/Distally-Positioned Stop Mechanism

The steps to use each of the subject systems of FIGS. 1, 2 and 3 are substantially the same or similar; however, dissimilarities in such steps will be identified in the following discussion.

After the patient has been properly prepped and a vascular access site has been created, such as in the femoral or carotid arteries, guide wire assembly 10 is delivered, without an attached filter, to a target vessel (not shown) using well-known percutaneous delivery techniques. The one-way translation member (i.e., 22 of FIG. 1, 60 of FIG. 2, 70 of FIG. 3) of proximal stop 20 is held in a restrained or constricted condition, such as within the lumen of delivery sheath 32 or pusher tube 44 (not shown) or, for the embodiment of FIG. 3, within the lumen of protective sheath 72, so as to provide a low profile when crossing the lesion, reducing the risk of dislodgement of emboli from the lesion site. One-way translation members 22, 60 and 70, respectively, are kept in such a restrained or constricted condition until after proximal stop 20 has at least crossed to the distal side of the target lesion. Preferably, proximal stop 20 is kept in a low profile condition until after the filter assembly 37 is positioned between distal stop 18 and proximal stop 20, upon which the one-way translation member may be deployed.

Once guide wire assembly 10 is operatively positioned within the target vessel, filter delivery, deployment and retrieval assembly 30 is advanced over guide wire 12 in the distal direction. With respect to the embodiments of FIGS. 1 and 2, assembly 30 is advanced through the lesion, passing over and constricting proximal stop mechanism 20 in an elongated, constricted state as it passes through the lumen of filter attachment tube 36 (see FIGS. 1B and 2B). Assembly 30 is further advanced until filter assembly 37 becomes completely positioned between distal stop 18 and proximal stop mechanism 20 (see FIG. 1C; not shown in FIG. 2). At this point, or once nose cone 34 abuts distal stop 18 (see FIG. 1D; not shown in FIG. 2), delivery sheath 32 may be pulled in the proximal direction (designated by arrow 46 of FIG. 1D) deploying filter 40 and leaving filter assembly 37 and pusher tube 44 stationary. As shown in FIGS. 1B-D and 2B, the filter assembly 37 is translated distally over guide wire 12 and is caused to pass over proximal stop 20, causing one-way translation member 22 or 60, respectively, to constrict and become retained within the lumen of filter attachment tube 36. After filter assembly 37 has been pushed completely to the distal side of proximal stop 20 by means of pusher tube 44 and delivery sheath 32, pusher tube 44 is then translated over proximal stop 20, causing one-way translation member 22 or 60 to enter into the lumen of pusher tube 44, maintaining proximal stop 20 in a low profile state as shown in FIG. 1C, for example.

Referring now to the embodiment of FIG. 3, one-way translation member 70 is delivered to the targeted location disposed within protective sheath 74, being held in a low profile state. Once the guide wire assembly 10 has been operatively positioned at a desired location within the vessel, delivery, deployment and removal assembly 30 is tracked over guide wire 12. Continued distal translation of assembly 30, as indicated by arrow 76 of FIG. 3B, will push protective sheath 74 distally of proximal stop 20 and cause proximal stop 20 to enter into the lumen of filter assembly 37, maintaining it in a low profile state.

Referring again to each of the embodiments of FIGS. 1, 2 and 3, at this point, filter assembly 37 is caused to pass over proximal stop 20 and be positioned between distal stop 18 and proximal stop 20, as shown in FIG. 1C, for example. Delivery sheath 32 is then retracted in the proximal direction, as indicated, for example, by arrow 46 of FIG. 1D, deploying filter 40.

The deployment of filter 40 involves the radial-like expansion of support hoop 45 and its sealing engagement against the internal vessel wall (not shown). This sealing engagement is sufficiently secure to retain filter 40 in the same location within the vessel, however, filter 40 may experience some distal migration if the pores of filter sac 51 become sufficiently occluded by emboli collected therein. If such occurs, filter assembly 37 may have to be retrieved and exchanged for another filter assembly. The delivery and filter deployment steps just described may be facilitated by fluoroscopic imaging and the use of one or more radiopaque elements located on assembly 30 such as at the distal end of sheath 32 or on nose cone 34.

After filter 40 has been deployed, pusher tube 44 is pulled in the proximal direction, designated by arrow 48 of FIG. 1E, for example, and removed from the vessel, thereby releasing proximal stop mechanism 20 from its constricted state, allowing it to return to its preformed configuration (see FIGS. 1E and 2A) or its original state (see FIG. 3C). As such, when guide wire 12 is moved in the distal direction, designated by arrow 53 of FIG. 1F, for example, while filter 40 is deployed, or when filter assembly 37 is caused to move in the proximal direction along guide wire 12 and abut against proximal stop mechanism 20, one-way translation member prevents further distal progression of guide wire 12 or further proximal progression of filter assembly 37, as the case may be.

With regard to the embodiments of FIGS. 1 and 2, the proximally-directed compression of one-way translation member 22 or 60 causes it to transform into an expanded, high profile state, as illustrated in FIGS. 1F and 2C, creating a barrier to further progression. More specifically, with respect to the embodiment of FIG. 1, when the distal progression of guide wire 12 or the proximal progression of filter assembly 37 is such that the distal ends 52 of wires 23 of one-way translation member 22 enter into the proximal end 54 of the lumen of tube 36, the "elbows" 50 of translation member 22 are caused to fold outwardly to form a cross-wise barrier, preventing any further distal translation of guide wire 12 or proximal translation of filter assembly 37, as illustrated in FIG. 1F. Filter assembly 37 is otherwise free to translate axially along guide wire 12 between distal stop 18 and proximal stop mechanism 20. The folded configuration of wires 23 also provides resistance to the unintentional crossing of the lesion by guide wire assembly 10 when guide wire 12 is pulled in the proximal direction.

With the embodiment of FIG. 2, when the distal progression of guide wire 12 or the proximal progression of filter assembly 37 is such that the biased spring force of coil 60 is overcome and caused to become fully compressed by filter assembly 37, a radial barrier is formed cross-wise to the longitudinal axis of guide wire 12, as shown in FIG. 2C. This barrier will prevent, under normal or typical forces used in such interventional procedures, the over-extension of guide wire 12 in the distal direction and the over-translation of filter assembly 37 in the proximal direction.

Unlike the one-way translation members of FIGS. 1 and 2, the original, biased position of lever member 70 provides the high profile state without any compressive force from filter assembly 37. In this original, biased position, lever member 70 will prevent, under normal or typical forces used in such an interventional procedure, the over-extension of guide wire 12 in the distal direction and the over-translation of filter assembly 37 in the proximal direction.

Upon completion of the interventional procedure, delivery sheath 32, now functioning as a filter retrieval sheath, is positioned over guide wire 12 and reinserted into the target vessel. Delivery sheath 32 is advanced distally until its open distal end 31 crosses the now-opened lesion. Delivery sheath 32 may then be further advanced over proximal stop mechanism 20, thereby causing proximal stop mechanism 20 to enter into distal end 31 and be positioned in its elongated state within delivery sheath 32. Delivery sheath 32 may then be advanced over filter assembly 37, causing support hoop 45 of filter 40 to fold and collapse, thereby sealing the contents captured within sac 51. Continued incremental advancement causes the entirety of filter assembly 37 to be positioned within distal end 31 of delivery sheath 32 and distal end 31 to abut the proximal end of nose cone 34. Alternatively, after the open distal end 31 of delivery sheath 32 has crossed to the distal side of the lesion, guide wire 12 and attached filter assembly 37 may be pulled proximally to withdraw and retrieve filter assembly 37 into the opening at distal end 31. Delivery sheath 32 and guide wire assembly 10 are now withdrawn from the target vessel. The vasculature access site may then be closed by many well-known techniques in the art.

In use, the system of FIG. 4 is deployed by placing guidewire 12 in a desired location within the patient. Sheath 30 including filter assembly 37 disposed therein is advanced distally along wire 12 until male threaded feature 24 engages female threaded feature 69 (FIG. 4B). Wire 12 is then rotated relative to delivery sheath 30 and filter 37 to further threadedly engage feature 24 with feature 69 until filter assembly 37 is disposed distally of male threaded feature 24 (FIG. 4C). Then sheath 30 is withdrawn proximally to allow filter 42 to expand (FIG. 4D).

B. Extended-Length Tubular Filter Attachment Sheath/Proximally-Positioned Stop Mechanism The steps necessary to use the subject system of FIGS. 5, 6 and 7 will now be described.

After the patient has been properly prepped and a vascular access site has been created, such as in the femoral or carotid arteries, guide wire assembly 10 of FIG. 5A is delivered, without an attached filter, to within a target vessel (not shown) using well-known percutaneous delivery techniques. Once guide wire assembly 10 is operatively positioned within the target vessel, filter delivery, deployment and retrieval assembly 78 is advanced over guide wire 12 in the distal direction, crossing the lesion to distal portion 14 of guide wire 12. Delivery sheath 86 maintains filter 82 in an undeployed state while it is being translated to distal portion 14, as shown in FIG. 5B. Delivery sheath 86 is then retracted in the proximal direction thereby deploying filter 90, as shown in FIG. 5C, at distal portion 14.

The deployment of filter 82 involves the radial-like expansion of support hoop 96 and its subsequent sealing engagement against the internal vessel wall (not shown). This sealing engagement is sufficiently secure to retain filter 82 in the same location within the vessel as desired; however, filter 90 may experience some unintentional distal migration if the pores of filter sac 92 become sufficiently occluded by emboli collected therein or during catheter exchanges. If such occurs, filter assembly 80 may have to be retrieved (to be described below regarding the removal of filter assembly 80) and exchanged for another filter assembly. The delivery and filter deployment steps just described may be facilitated by fluoroscopic imaging and the use of one or more radiopaque elements located on filter assembly 80 such as at the distal end of attachment sheath 82 or on nose cone 85.

Once filter 82 is operatively deployed within the subject vessel, the position of filter 82 may releasably locked or fixed with respect to the guide wire. To fix the position, or otherwise limit or prevent at the translation of filter 82, extended-length attachment sheath 90 may be releasably locked to guide wire 12 by means of a stop mechanism, such as those of FIGS. 6 and 7, located at a proximal portion of guide wire 12. The locking process includes disposing a sleeve, 104 or 116 of FIGS. 6 and 7, respectively, about guide wire 12 and the proximal end of attachment sheath 90. The sheath is made to firmly retain the proximal end of the sheath within the sleeve. Using the proximal stop mechanism of FIG. 6 for this purpose involves inserting at least a portion 122 of the proximal end 98 of sheath 90 into the distal opening of sleeve 104 that provides sufficient compression on portion 122 to firmly hold it in place. Using the proximal stop mechanism of FIG. 6 involves positioning a distal portion of sheath 90 over a threaded portion 114 of guide wire 12 and then threading a threaded sleeve 116 over threaded portion 114, thereby firmly retaining sheath 90 between guide wire 12 and sleeve 116. Alternately, attachment sheath 90 may be manually held at its proximal end in order to fix the position of the embolic filter. Sheath 90 may be unlocked as desired to reposition or remove the embolic filter.

The interventional procedure(s) may then be performed by interventional instruments, such as angioplasty catheters, atherectomy devices, stent delivery systems or intravascular diagnostic instruments advanced along guide wire 12 to the targeted treatment site(s). During the selected interventional procedure(s), emboli or thrombi released from the treatment site are collected or filtered by filter 82 while blood is allowed to flow unimpeded in the downstream direction.

Upon completion of the interventional procedure, the embolic filter assembly 80 may be removed from the vessel.

A delivery sheath 78, now functioning as a filter retrieval sheath, is positioned over guide wire 12 and extended-length attachment sheath 90 and reinserted into the target vessel. Delivery sheath 78 is advanced through the now-opened lesion and over filter assembly 80, causing support hoop suspension strut 94 and support hoop 96 of filter 82 to fold and collapse, thereby sealing the contents captured within sac 51. Alternatively, after the open distal end 87 of delivery sheath 78 has crossed to the distal side of the lesion, guide wire 12 and filter assembly 80 may be pulled proximally to withdraw and retrieve filter assembly 80 into the opening at distal end 87. Either before or after reinsertion of sheath 78, sheath 90, if locked at the time, is unlocked. Delivery sheath 78, filter assembly 80 and guide wire assembly 10 are then withdrawn from the target vessel. The vasculature access site may then be closed by techniques well-known in the art.

C. Repositioning and Adjusting the Filter Assembly and/or the Guide Wire

During the course of positioning and deploying the subject filters, as well as during the interventional procedure being performed, various situations may arise wherein it is necessary to correct or readjust the position of the filter or of the guide wire or of both within the vessel. For example, the initial positioning and deployment of the filter may not be optimal as it may have been unintentionally deployed over the opening to a side branch vessel, thereby blocking blood flow to the side branch vessel. The filter may have been deployed in a location of the vessel that has an inappropriate diameter size that will not allow proper engagement between the filter support loop and the internal vessel wall. Also, the section of vessel in which the filter is deployed may have plaque that is easily dislodged upon deployment.

Furthermore, adjustment of the filter may be required for reasons other than for a non-optimal deployment location. For example, as the filter sac collects emboli it becomes more resistant to blood flow. In time, particularly with respect to the filter assembly embodiments employing a shorter-length attachment sheath which are capable of some axial translation between proximal and distal stop mechanisms, as well as with an unlocked extended-length embodiment, the increase in pressure on the filter sac may cause the filter assembly to migrate in a distal direction and require readjustment of its position. Also, the filter may be unintentionally moved proximally or distally by the common and sometimes necessary manipulation of the guide wire, for example, in the exchange of interventional instruments within the vessel. All of the above circumstances may require adjusting the position of the filter or the guide wire or both within the vessel, either in the proximal or distal direction, during the course of the procedure.

In addition to the axial translation of the filter and/or guide wire, some rotational movement of either or both may be necessary or unavoidable. During delivery of the filter assembly, or before or after deployment of the filter, the guide wire may be forced to rotate due to the anatomy of the vessel or there may otherwise be a need to rotate guide wire. For example, as the guide wire advances through a tortuous section of vessel, some intentional or unintentional rotation of the guide wire may occur. If such rotational movement does occur, the filter, when undeployed, will maintain its rotational position within the delivery sheath through which it is delivered. Maintaining its position during delivery minimizes the risk of the filter sac becoming entangled with the support hoop and the attachment sheath. When the filter is in a deployed state, its ability to maintain its rotational position within the vessel minimizes the chance of scraping the vessel wall and of dislodging the support hoop possibly creating an improper engagement between it and the vessel wall.

III. Kits

Also provided by the subject invention are kits for use in practicing the subject methods. A kit of the subject invention includes at least one subject guide wire assembly and at least one subject filter delivery, deployment and removal assembly. Other kits may include two or more subject guide wire assemblies 10 without an accompanying filter delivery, deployment and removal assembly 30. The guide wire assemblies may have respective guide wires of varying dimensions, such as varying lengths. For those kits having embolic filter system embodiments employing shorter-length filter attachment sheaths (i.e., as disclosed in FIGS. 1, 2, 3, and 4), multiple guide wire assemblies may be provided having varying separation distances between proximal and distal stops. Kits containing an embolic filter system embodiments employing extended-length filter attachment sheaths (i.e., as disclosed in FIGS. 1, 6 and 7), multiple filter assemblies may be provided having varying attachment sheath lengths. Certain kits may also include one or more vascular interventional systems, such as an angioplasty system, along with a subject guide wire assembly 10 and a subject filter delivery, deployment and removal assembly 30. Finally, the subject kits preferably include instructions for using the subject device(s) and system(s) during an interventional procedure to protect the patient against emboli. These instructions may be present on one or more of the instructions for use included in the kits, packaging, label inserts or containers present in the kits, and the like.

IV. Advantages of the Subject Invention

Another advantage of the axial translation limitation system of the present invention is that the configuration of the proximal and distal stops is such that a low-profile guide wire assembly 10 can be maintained during delivery and retrieval of the guide wire assembly, making the initial crossing of the lesion easier and safer. This feature is particularly advantageous when the vessel at the lesion site is close to being occluded.

Still another advantage of the present invention is that guide wire 12 can make the first crossing of the lesion without the added profile of an attached filter, thereby reducing the risk of friction between the guide wire assembly and the lesion site and thereby minimizing the risk of embolization of plaque from the lesion site.

The combination of the movement systems and the movement limitation systems of the present invention provide flexibility and ease of use of the subject devices and systems, and reduce the risks (e.g., the lack of a proper sealing engagement between the internal vessel wall and the deployed filter, device profiles which are too large or angular to cross safely over the lesion, the unintentional movement of the filter while deployed, the distal migration of the filter off the distal tip of the guide wire, the proximal migration of the filter into the lesion site, etc.) involved in intravascular procedures.

Thus, it is evident from the above description that the subject inventions provide a significant contribution to the field of embolic protection. The subject invention has been shown and described herein in what is considered to be the most practical, and preferred embodiments. It is recognized, however, that departures may be made there from, which are within the scope of the invention, and that obvious modifications will occur to one skilled in the art upon reading this disclosure. Such departures and modifications that come within the meaning and range of equivalents of the disclosed concepts, are intended to included within the scope of the appended claims.

What is claimed:

1. An intravascular embolic protection system comprising:
   a guidewire;
   a filter having a proximal end and a distal end, the filter coupled to a tubular member, the tubular member extending at least from the proximal end of the filter to the distal end of the filter, the tubular member being slidably engageable over the guidewire; and
   a first stop member coupled to the guidewire and located proximal to the tubular member when the tubular member is operatively engaged over the guidewire, the first stop member including a helical region that is disposed about the guidewire.

2. The system of claim 1, wherein the first stop member comprises a coil having a distally increasing diameter.

3. The system of claim 1, wherein the first stop member includes a male threaded feature.

4. The system of claim 1, wherein the first stop member has a substantially fixed configuration.

5. The system of claim 1, wherein the first stop member has a naturally-biased, high profile position and an unbiased, low profile position.

6. The system of claim 1, further comprising a second stop member located distal to the tubular member when the tubular member is operatively engaged over the guidewire.

7. An intravascular embolic protection system for collecting and removing debris from within a vessel, comprising:
   a filter attached to a tubular sheath, the tubular sheath comprising an open distal end, an open proximal end, and a guidewire lumen extending therebetween, wherein the guidewire lumen has a length that is substantially the same as or greater than a length of the filter;
   a guidewire operatively disposed within the guidewire lumen, the guidewire having a proximal region and a distal region; and
   a stop member coupled to the distal region of the guidewire, the stop member including a helical region that is disposed about the guidewire.

8. The system of claim 7, wherein the stop member comprises a coil having a distally increasing diameter.

9. The system of claim 7, wherein the stop member includes a male threaded feature.

10. The system of claim 7, wherein the stop member has a substantially fixed configuration.

11. The system of claim 7, wherein the stop member has a naturally-biased, high profile position and an unbiased, low profile position.

12. The system of claim 7, further comprising a second stop member located distal to the tubular sheath when the guidewire is operatively disposed within the guidewire lumen.

* * * * *

UNITED STATES PATENT AND TRADEMARK OFFICE
CERTIFICATE OF CORRECTION

PATENT NO. : 7,648,518 B2  Page 1 of 1
APPLICATION NO. : 11/219033
DATED : January 19, 2010
INVENTOR(S) : Salahieh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this

Twenty-third Day of November, 2010

David J. Kappos
*Director of the United States Patent and Trademark Office*